(12) United States Patent
Wyrwa et al.

(10) Patent No.: US 12,129,222 B2
(45) Date of Patent: Oct. 29, 2024

(54) PRODUCTION OF BITTER PRINCIPLE DERIVATIVES

(71) Applicant: Julius-Maximilians-Universitaet Wuerzburg, Wuerzburg (DE)

(72) Inventors: Ralf Wyrwa, Rothenstein (DE); Claudia Rode, Jena (DE); Thomas Seemann, Bucha (DE); Lorenz Meinel, Wuerzburg (DE); Jennifer Ritzer, Estenfeld (DE); Matthias Schnabelrauch, Jena (DE)

(73) Assignee: Julius-Maximilians-Universitaet, Wuerzburg (DE)

( * ) Notice: Subject to any disclaimer, the term of this patent is extended or adjusted under 35 U.S.C. 154(b) by 441 days.

(21) Appl. No.: 16/324,758

(22) PCT Filed: Aug. 11, 2017

(86) PCT No.: PCT/EP2017/070450
§ 371 (c)(1),
(2) Date: Feb. 11, 2019

(87) PCT Pub. No.: WO2018/029347
PCT Pub. Date: Feb. 15, 2018

(65) Prior Publication Data
US 2019/0185416 A1    Jun. 20, 2019

(30) Foreign Application Priority Data
Aug. 11, 2016    (DE) ............ 10 2016 009 766.3

(51) Int. Cl.
| | |
|---|---|
| C07C 237/04 | (2006.01) |
| A61K 47/18 | (2017.01) |
| A61K 47/54 | (2017.01) |
| A61K 47/65 | (2017.01) |
| C07C 231/12 | (2006.01) |
| C07C 233/07 | (2006.01) |
| C07C 269/04 | (2006.01) |

(52) U.S. Cl.
CPC .......... C07C 237/04 (2013.01); A61K 47/186 (2013.01); A61K 47/54 (2017.08); A61K 47/65 (2017.08); C07C 231/12 (2013.01); C07C 233/07 (2013.01); C07C 269/04 (2013.01)

(58) Field of Classification Search
None
See application file for complete search history.

(56) References Cited

U.S. PATENT DOCUMENTS

| | | | | |
|---|---|---|---|---|
| 5,273,885 | A * | 12/1993 | Visor ................ | G01N 33/78 435/7.9 |
| 8,273,542 | B2 * | 9/2012 | Li .................... | G01N 33/566 436/501 |
| 2013/0091610 | A1 * | 4/2013 | Hennessey, IV ...... | B63C 11/04 2/2.15 |

FOREIGN PATENT DOCUMENTS

| | | |
|---|---|---|
| GB | 1 307 250 A | 2/1973 |
| WO | WO 2005/063777 A1 | 7/2005 |
| WO | WO 2013/132058 | 9/2013 |

OTHER PUBLICATIONS

CAS registry No. 1605618-01-6, May 16, 2014, 1 page (Year: 2014).*
Ilieva et al. ('Computational study of the aminolysis of esters the reaction of methylformate with ammonia' J Org Chem v68 2003 pp. 1496-1502) (Year: 2003).*
Saroli A ('Interaction of denatonium chloride with the bitter taste receptor' Z Lebensm Unters Forsch v180 1985 pp. 227-229) (Year: 1985).*
Alfred Saroli, "Structure-Activity Relationship of Bitter Compounds Related to Denatonium Chloride and Dipeptide Methyl Esters", Zeitschrift Fuer Lebensmitteluntersuchung Und-Forschung, vol. 182 (2): pp. 118-120 (Feb. 1, 1986) (Abstract Only).
Database Z-Registry: Accession No. 1605618-01-06 (May 16, 2014).
Database Z-Registry: Accession No. 1597451-18-7 (May 5, 2014).
Database Z-Registry: Accession No. 1595199-59-9 (May 1, 2014).
Database Z-Registry: Accession No. 1578182-21-4 (Apr. 1, 2014).
Database Z-Registry: Accession No. 1575693-30-9 (Mar. 28, 2014).

* cited by examiner

*Primary Examiner* — Ronald T Niebauer
(74) *Attorney, Agent, or Firm* — Smith Patent, LLC; Chalin A. Smith

(57) ABSTRACT

It is an object of the present invention to introduce carboxylic acid-functionalities suitable for coupling into the denatonium structure by means of simple synthesis, namely the synthesis of bitter principle derivatives based on the denatonium structure according to formula 1:

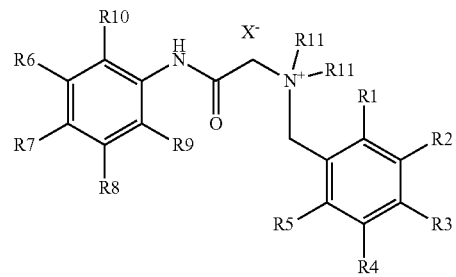

Formula 1

For example, according to the invention, lidocaine derivatives may be reacted with carboxylated benzyl halogenides. The carboxylated denatonium derivatives of the present invention are especially applied in medicine, biology, medical engineering as well as cosmetics, the pharmaceutical, chemical, and foodstuff industry.

3 Claims, No Drawings
Specification includes a Sequence Listing.

PRODUCTION OF BITTER PRINCIPLE DERIVATIVES

PRIORITY

This application corresponds to the U.S. national phase of International Application No. PCT/EP2017/070450, filed Aug. 11, 2017, which, in turn, claims priority to German Patent Application No. 10 2016 009 766.3 filed Aug. 11, 2016, the contents of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Nov. 19, 2021, is named LNK200US_SL.txt and is 1,717 bytes in size.

FIELD OF THE INVENTION

The synthesis of bitter principle derivatives by introducing groups suitable for coupling into the denatonium structure is described. The synthesis permits the generation of a number of substitution patterns. The invention serves to provide bitter principle derivatives for applications in medicine, biology, medical engineering as well as in cosmetics, pharmaceutical, chemical, and foodstuff industry.

BACKGROUND OF THE PRESENT INVENTION

There are a number of natural bitter principles from the classes of substances of the glycosides, isoprenoids, alkaloids, and peptides [S. Rodgers et al., Chem. Senses 30, 2005, 547-557; A. Troszyńska, Pol, J. Food Nutr. Sci. 13/54, 2004, 65-73; A. Drewnowski et al., Am. J. Clin. Nutr. 72, 2000, 1424-1435]. These bitter principles are naringin, cucurbitacin, lactucopicrin, premarrubiin, marrubiin, cynarine, lactucin, caffeine, theobromine, quinine, and cinchonidine. The most bitter natural substance is amarogentin from the gentian root. Also, so far a number of synthetic bitter principles have been produced. These are, for example quaternary ammonium compounds [A. Saroli, Z Lebensm Unters Forsch 182, 1986, 118-120]. Here, the most bitter substance is benzyldiethyl(2,6-xylylcarbamoyl)methylammonium benzoate that is also known as denatonium benzoate, Bitrex®, Aversion® [EP 0955309 A1]. Here, the bitter constituent is the benzyldiethyl(2,6-xylylcarbamoyl)-methylammonium ion. Therefore, also the commercial denatonium saccharinate or also capsaicinate [U.S. Pat. No. 5,891,919A] are strongly bitter substances. As a bitter principle denatonium is used in various fields of application. Denatonium benzoate is used for example to denaturize ethanol, so that the alcohol is no longer suitable for human consumption. Also other alcohols as well as solvents, detergents, shampoos, soaps are mixed with denatonium benzoate to avoid damage to health caused by their oral ingestion. The bitter principle is also used as an additive in nail polish against fingernail biting. Since rats do not perceive denatonium benzoate at low concentrations it is also a suitable safety additive in rat poison.

Despite a number of natural and synthetic bitter principles a covalent binding of bitter principles for the development of further fields of application so far is an unsolved problem. By derivatization the substances usually lose their bitter taste. Moreover, derivatization of natural bitter principles is uneconomic because isolation of these substances from plants is a cost-intensive process. Also, a number of natural substances is unsuitable for chemical derivatization since either suitable functionalities are missing or the substances are decomposed during synthesis.

Therefore, there is an urgent need for bitter principles that allow a simple derivatization with various residues. Here, synthesis of such substances is to be reproducibly practicable in a simple method, cost-effective and in technical scale to meet the growing demand from medicine, biology, medical engineering as well as cosmetics, pharmaceutical, chemical, and foodstuff industry.

SUMMARY OF THE INVENTION

The Present Invention Relates to:
1. A compound of general formula 1

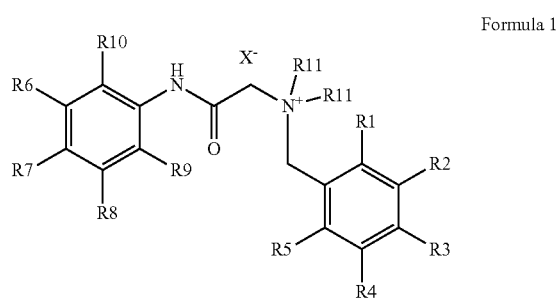

Formula 1 wherein

X⁻ represents halogenide, pseudo-halogenide, sulphate, benzoate, acetate, trifluoroacetate, hydroxide, saccharinate, or capsaicinate, R1-R10 independently represent hydrogen, halogen, C1-C5 alkyl, C1-C4 alkoxy, C1-C20 alkoxycarbonyl, —NH—P, —O—P, wherein P is a hydrogen, a peptide residue or a peptide residue consisting of 1-30 amino acids (wherein these can be modified and unmodified D-amino acids, L-amino acids as well as unnatural amino acids), which is modified for coupling, —(Y)$_n$— —COOR13, —(Y)$_n$—COOM with M=Na, K, [N(R12)$_4$]⁺, or —(Y)$_n$—C(O)NR14R15, wherein R14 and R15 represent hydrogen, a C1-C12 alkyl or a peptide residue consisting of 1-30 amino acids (wherein these can be modified and unmodified D-amino acids, L-amino acids as well as unnatural amino acids), wherein at least one of the residues R1-R10 is a group —(Y)$_n$—COOM, —(Y)$_n$—COOR13 or —(Y)$_n$—C(O)NR14R15, wherein Y represents an organic residue and n=0 or 1, and R11, R12, R13 independently represent hydrogen or a C1-C10 alkyl residue.

2. The compound according to item 1, wherein in the general formula 1 residue R11 is an ethyl group, residues R9, R10 are methyl groups, residues R1, R4, R5, R6, R7, R8 represent hydrogen, one of residues R2 and R3 represents hydrogen and the other —(Y)$_n$—COOR13, —(Y)$_n$—COOM with M=Na, K, [N(R12)$_4$]⁺, or —(Y)$_n$—C(O)NR14R15, or residues R2 and R3 independently represent —(Y)$_n$—COOR13, —(Y)$_n$—COOM with M=Na, K, [N(R12)$_4$]⁺, or —(Y)$_n$—C(O)NR14R15, wherein residues R14 and R15 independently represent hydrogen, a C1-C12 alkyl or a peptide residue consisting of 1-30 amino acids (wherein these can be modified and unmodified D-amino acids, L-amino acids as well as unnatural amino acids), Y represents an organic residue, wherein n=0 or 1, and residues R12, R13 independently represent hydrogen or a C1-C10 alkyl residue.

3. A substrate comprising a compound according to item 1 or 2, characterized in that the compound is bound to a surface of metal, ceramics, glass, or polymeric material, wherein the polymeric material is preferably a resin, via a peptide residue or a hydrocarbon residue of the compound, optionally via an additional linker group, especially a peptide, polyester, polyamide, hydrocarbon or polyethylene glycol linker group.

4. A method for preparing a compound according to item 1 or 2, characterized in that the starting compounds of formula 2 and formula 3

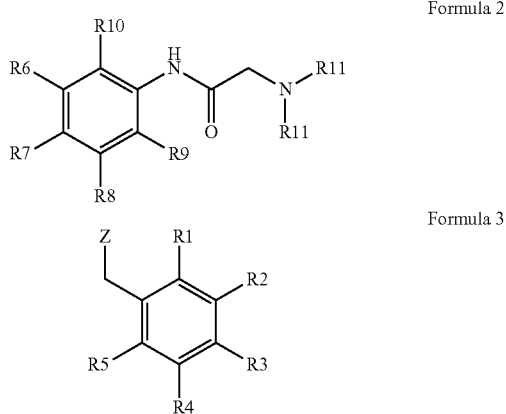

Formula 2

Formula 3 are reacted with each other in a solid or dissolved form, wherein Z in formula 3 represents a substitutable group, especially a halogen atom or a tosylate group, and residues R11 and R1-R10 have the meaning defined in item 1 or 2.

5. The method according to item 4, characterized in that the molar ratio of the starting compounds of formula 2 and formula 3 is 1:1 and/or the reaction is performed at a temperature of 20-200° C., preferably at 20-80° C., and the reaction is performed in the presence or absence of a solvent, wherein the optional solvent is an organic solvent or water.

6. The method according to item 4 or 5, characterized in that both starting compounds of formula 2 and formula 3 are blended in a solid form at room temperature (20 to 30° C.) and are reacted in absence of a solvent.

7. The method according to item 4 or 5, characterized in that the starting compounds of formula 2 and formula 3 are reacted in a microwave-assisted reaction within 1 h, wherein the microwave-assisted reaction is performed in a solvent.

8. The method for preparing a substrate according to item 3, characterized in that the starting compounds of formula 2 and formula 3, as defined in item 4, are reacted with each other in a solvent, wherein one of the starting compounds of formula 2 and formula 3 is bound to a solid phase and the other starting compound of formula 2 and formula 3 is in solution, wherein the solid phase bond is achieved via one of residues R1-R10, optionally via an additional linker group, especially a peptide, polyester, polyamide, hydrocarbon, or polyethylene glycol linker group, and the solid phase is metal, ceramics, glass, or a polymeric material, wherein the polymeric material preferably is a resin.

9. Use of a compound according to one of items 1-2 as a flavouring substance, especially as a bitter principle.

10. Use according to item 9 in medicine, biology, medical engineering as well as in cosmetics, pharmaceutical, chemical, and foodstuff industry.

DETAILED DESCRIPTION OF THE PREFERRED EMBODIMENTS

Therefore, the invention is based on the problem to produce bitter principles in a simple manner that contain at least one functional group, in the derivatization of which the bitter taste is maintained or the bitter taste occurs by suitable hydrolytic or enzymatic cleavage. According to the invention this problem is solved by suitably reacting 2-diethyl-amino-N-(2,6-dimethylphenyl)acetamide (lidocaine) or a functionalized lidocaine derivative with benzylhalogenide derivatives to compounds of general formula 1.

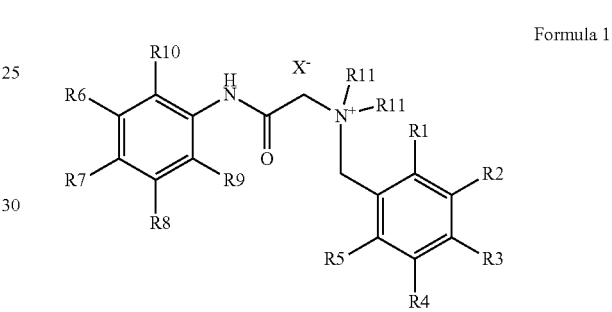

Formula 1

Here, $X^-$ in formula 1 for example represents halogenide, pseudo-halogenide, sulphate, benzoate, acetate, trifluoroacetate, hydroxide, saccharinate, or capsaicinate. Preferably, $X^-$ is a halogenide and particularly preferred $Cl^-$, $Br^-$, or $I^-$.

In formula 1 R1-R10=H, halogen, a C1-C5 alkyl, C1-C4 alkoxy, C1-C20 alkoxycarbonyl, NH—P, O—P, wherein P is hydrogen, a peptide residue or a peptide residue consisting of 1-30 amino acids (modified and unmodified D-amino acids, L-amino acids as well as unnatural amino acids as defined in the "World Intellectual Property Organization (WIPO) Handbook on Industrial Property Information and Documentation, Standard ST.25 (1998), including Tables 1 through 6 of Appendix 2"), which is modified for coupling, —(Y)$_n$—COOR13, —(Y)$_n$—COOM with M=Na, K, [N(R12)$_4$]$^+$, or —(Y)$_n$—C(O)NR14R15 group, wherein R14 and R15=H, a C1-C12 alkyl or a peptide residue consisting of 1-30 amino acids (WIPO), wherein at least one of residues R1-R10 is a group —(Y)$_n$—COOM, —(Y)$_n$—COOR13 or —(Y)$_n$—C(O)NR14R15.

Y represents an organic residue such as for example —CH$_2$—, —CH(CH$_3$)—, —CH$_2$—CH$_2$—, —(CH$_2$)$_3$—, —CH=CH—, —C≡C—, —O—CH$_2$—CH$_2$—, —O—CH$_2$—CH$_2$—O—CH$_2$—CH$_2$—, —NH—CH$_2$—CH$_2$—, without limitation, wherein n=0 or 1.

R11, R12, R13 independently represent H or a C1-C10 alkyl residue.

Preferably, R1-R5, R6-R10=H, a methyl, ethyl, methoxy, ethoxy, carboxyl, methoxycarbonyl, ethoxycarbonyl or —(Y)$_n$—C(O)NR14R15 group with R14=H and R15=C1-C12 alkyl or a peptide residue consisting of 1-30 amino acids (according to the previous definition), wherein one of residues R1-R5, R6-R10 represents a —(Y)$_n$—COOR13, —(Y)$_n$—COOM or —(Y)$_n$—C(O)NR14R15 group.

Particularly preferred R1-R5=H and one of residues R1-R3 is a group —(Y)$_n$—COOR13, —(Y)$_n$—COOM or —(Y)$_n$—C(O)NR14R15.

Particularly preferred R6-R8=H and R9-R10=methyl, if at least one of residues R1-R5 is a group —(Y)$_n$—COOM, —(Y)$_n$—COOR13 or —(Y)$_n$—C(O)NR14R15.

Preferably, R11 is a C1-C8 alkyl residue such as e.g. a methyl, ethyl, n-propyl, i-propyl, n-butyl group.

Particularly preferred R11 is a methyl, ethyl, or propyl group.

Already known is to synthesize denatonium salts starting from lidocaine and benzylbromide in suitable solvents such as alcohols, water in a reaction of several hours of 20-24 hrs at an elevated temperature between 50-100° C. [WO2006062406 A2]. For the preparation of such compounds also an amide coupling of corresponding educts Ph-NH$_2$ and Ph-CH$_2$—NR$_2$—CH$_2$COX1 (X1=halogen, OH) or ammonium formation starting from Ph-NH—CO—CH$_2$—Hal (Hal=halogen) and Ph-CH$_2$—NR$_2$ would be conceivable, but which in both variants is only possible via long synthesis pathways and low total yields.

It was surprisingly found that carboxylated and carboxyalkyl-substituted (-alkyl—COOR) benzylhalogenides with lidocaine in a molar ratio of 1:1 already at low temperatures of 20-80° C. in a suitable solvent react to the corresponding carbon acid derivatives of denatonium. Also, a microwave-assisted reaction in a suitable solvent for preparing substances according to formula 1 at temperatures up to 200° C. and reaction times of max. 60 min is suitable for the synthesis. Still more surprising was the result that the solid substances also react without using solvents after combination at room temperature and that the spontaneous reaction is completed with high yields with short reaction times of only a few minutes. In this way, carboxyl-functionalized denatonium derivatives are obtained that can be further reacted by means of suitable synthesis to salts, esters, and amides.

Moreover, it was also surprisingly found that the carboxyl-functionalized denatonium derivatives have an intensive bitter taste, whereas changes in the denatonium basic structure lead to a loss of the bitter taste.

Advantageous for the synthesis of the carboxyl-functionalized denatonium derivatives is the low technical and energetic expenditure, since either no solvents are needed and in general a reaction control at room temperature is sufficient or only short reaction times in the microwave-assisted reaction are needed. The products are characterized by a high purity, which eliminates the need for costly cleaning.

The uncomplicated production of carboxylated denatonium derivatives makes it possible to provide such substances in larger quantities.

MODES FOR CARRYING OUT THE INVENTION

In a preferred embodiment of the invention one of both educts (lidocaine or benzyl halogenide derivative) is added to the reaction vessel in a solid form. The second component is added at room temperature in a solid form. After short mixing, a spontaneous reaction starts, wherein the solid substances form a melt. The reaction is controlled by means of thin layer chromatography. In most cases, the reaction is completed within 10-120 min. The reaction can also be performed in a suitable solvent such as an organic solvent or water at room temperature or short-term moderate heating. Another option is the microwave-assisted reaction up to 200° C. with reaction times of max. 1 hr. Purification of the substances, if needed, can be performed by means of re-crystallization or column chromatography. For further derivatization suitable denatonium derivatives are reacted to salts, esters, and amides according to methods known to the skilled person.

Testing the bitter taste of synthesized compounds compared to denatonium benzoate can be performed for example with an electronic tongue, wherein the electric potentials of aqueous substance solutions of a defined concentration are determined in accordance with methods known to the skilled person.

Like amino acids denatonium derivatives can be coupled to an immobilized amino acid chain (bound to a polymeric carrier (resin)) of any length by means of solid phase peptide synthesis (SPPS). In the synthesis, the so-called Fmoc chemistry with HOBt (1-hydroxybenzotriazole) and DIPEA (N,N-diisopropylethylamine) as an auxiliary base is applied. First, HOBt forms an active ester from the carboxyl group of the Fmoc amino acid to be bound that then reacts with amines to a peptide bond. The Fmoc cleavage is performed with piperidine in dimethylformamide (DMF).

After coupling, the protective groups and the construct consisting of denatonium derivative and peptide are simultaneously cleaved-off from the carrier with the addition of TFA. Reactive carbocations formed during the cleavage are quenched by the scavengers ethane dithiol, metacresol, and thioanisole.

Subsequently, the denatonium derivative/peptide construct cleaved-off from the carrier is precipitated in ice-cold ether and after centrifugation the solution is removed from the construct pellet.

Coupling can be verified by means of mass spectrometry (electrospray ionization (ESI) or matrix-assisted laser desorption/ionization (MALDI)).

The following examples are to explain the invention in more detail without limiting it.

EXAMPLES

Example 1

Reaction of lidocaine with 4-(bromomethyl)benzoic acid methyl ester A small excess of 4-(bromomethyl)benzoic acid methyl ester (18 mg, 80 µmol) was added to 17 mg of lidocaine (72.5 µmol) and it was suspended in 3 ml of water. The suspension is left for 30 min at 200° C. in the microwave. Subsequently, the solution is concentrated to a small volume and taken up in 1 ml of THE. The white solid formed is filtered off and washed with THE. 2-(2,6-Dimethylphenylamino)-N,N-diethyl-N-(4-(methoxycarbonyl)benzyl)-2-oxoethane ammonium bromide is obtained.

Example 2

Reaction of Lidocaine with 4-(bromomethyl)benzoic Acid 1 g of lidocaine (4.3 mmol) was mixed with 0.92 g (4.3 mmol) of 4-(bromomethyl)benzoic acid while shaking. To complete the reaction it was heated for 20 Minutes to 50° C. Subsequently, 10 ml of THF were added and stirred. The white precipitate formed was filtered off, washed with THF and dried. The substance was separated from the by-product lidocaine-4-(bromomethyl)benzoate formed by column chromatography and N-(4-carboxybenzyl)-2-(2,6-dimethylphenylamino)-N,N-diethyl-2-oxoethane ammonium bromide was obtained.

Example 3

Synthesis of 2-(2,6-dimethylphenylamino)-N,N-diethyl-N-(3-(methoxycarbonyl)benzyl)-2-oxoethane Ammonium Bromide 1 g of lidocaine (4.3 mmol) is combined with 0.98 g (4.3 mmol) of 3-(bromomethyl)benzoic acid methyl ester and shaken several times at room temperature within 10 minutes after having been added. Subsequently, 10 ml of THE are added and stirred. The white precipitate formed is filtered off, washed with THE and dried. 2-(2,6-Dimethylphenylamino)N,N-diethyl-N-(3-(methoxycarbonyl)benzyl)-2-oxoethane ammonium bromide is obtained. m.p.: 183-184° C.

MS (ESI): m/z=383.233 Da $(C_{23}H_{31}N_2O_3)^+$ $^1$H-NMR (DMF-D7, ppm): 1.61-1.64 (t, 6H, 2×CH$_3$); 2.32 (s, 6H, 2×CH$_3$); 2.73-2.78; 2.91-2.95 (CH$_3$, DMF-D7); 3.52 (H$_2$O in DMF); 3.71-3.81 (m, 4H, 2×CH$_2$); 3.94 (s, 3H, O—CH$_3$); 4.68 (s, 2H, CH$_2$); 5.20 (s, 2H, CH$_2$); 7.13-7.16 (m, 3H, 3×CH); 7.72-7.75 (t, 1H, CH); 8.03 (CH, DMF); 8.08-8.10 (d, 1H, CH); 8.16-8.18 (d, 1H, CH); 8.38 (s, 1H, CH); 10.87 (s, 1H, NH)

$^{13}$C-NMR (DMF-D7, ppm): 8.54 (CH$_3$); 18.77 (CH$_3$); 29.59-30.60 (DMF-D7); 34.73-35.73 (DMF-D7); 52.69 (O—CH$_3$); 55.39 (CH$_2$); 56.66 (CH$_2$); 62.11 (CH$_2$); 127.80 (CH); 128.60 (CH); 129.46 (C); 130.26 (CH); 131.52 (C); 131.75 (CH); 134.55 (CH); 134.62 (C); 136.08 (C); 138.56 (CH); 162.60-162.92 (DMF-D7); 163.45 (C); 166.55 (C)

Example 4

Synthesis of 2-(2,6-dimethylphenylamino)-N,N-diethyl-N-(4-(methoxycarbonyl)benzyl)-2-oxoethane Ammonium Bromide 1 g of lidocaine (4.3 mmol) is combined with 0.98 g (4.3 mmol) of 4-(bromomethyl)benzoic acid methyl ester and shaken several times at room temperature within 20 minutes after having been added. Subsequently, 10 ml of THE are added and stirred. The white precipitate formed is filtered off, washed with THE and dried. 2-(2,6-Dimethylphenylamino)N,N-diethyl-N-(4-(methoxycarbonyl)benzyl)-2-oxoethane ammonium bromide.

m.p.: 176-178° C.

$^1$H-NMR (DMF-D7, ppm): 1.61-1.64 (t, 6H, 2×CH$_3$); 2.31 (s, 6H, 2×CH$_3$); 2.73-2.78; 2.90-2.95 (CH$_3$, DMF-D7); 3.53 (H$_2$O in DMF); 3.74-3.82 (m, 4H, 2×CH$_2$); 3.96 (s, 3H, O—CH$_3$); 4.72 (s, 2H, CH$_2$); 5.16 (s, 2H, CH$_2$); 7.12-7.17 (m, 3H, 3×CH); 7.97-7.98 (d, 2H, 2×CH); 8.03 (CH, DMF); 8.10-8.11 (d, 2H, 2×CH); 10.88 (s, 1H, NH)

$^{13}$C-NMR (DMF-D7, ppm): 8.83 (CH$_3$); 18.95 (CH$_3$); 29.76-30.76 (DMF-D7); 34.89-35.89 (DMF-D7); 52.89 (O—CH$_3$); 55.90 (CH$_2$); 57.18 (CH$_2$); 62.22 (CH$_2$); 127.94 (CH); 128.74 (CH); 130.48 (CH); 132.40 (C); 133.80 (C); 134.51 (CH); 134.75 (C); 136.23 (C); 162.62-163.09 (DMF-D7); 163.55 (C); 166.73 (C)

Example 5

Synthesis of 2-(2,6-dimethylphenylamino)-N,N-diethyl-N-(4-(methoxycarbonyl)benzyl)-2-oxoethane Ammonium Chloride 1 g of lidocaine (4.3 mmol) is combined with 0.79 g (4.3 mmol) of 4-(chloromethyl)benzoic acid methyl ester and shaken several times at room temperature within 20 minutes after having been added. Subsequently, 10 ml of THE are added and stirred. The white precipitate formed is filtered off, washed with THE and dried. 2-(2,6-Dimethylphenylamino)N,N-diethyl-N-(4-(methoxycarbonyl)benzyl)-2-oxoethane ammonium chloride is obtained.

Example 6

Synthesis of 2-(2,6-dimethylphenylamino)-N,N-diethyl-N-(4-(2-methoxy-2-oxoethyl)benzyl)-2-oxoethane Ammonium Bromide 0.3 g of lidocaine (1.3 mmol) are combined with 0.31 g (1.3 mmol) of methyl-2-(4-(bromomethyl)phenyl)acetate and shaken several times at room temperature within 20 minutes after having been added. Subsequently, 10 ml of THE are added and stirred. The white precipitate formed is filtered off, washed with THE and dried. 2-(2,6-Dimethylphenylamino)N,N-diethyl-N-(4-(2-methoxy-2-oxoethyl)benzyl)-2-oxoethane ammonium bromide is obtained.

$^1$H-NMR (DMF-D7, ppm): 1.59 (m, 6H, 2×CH$_3$); 2.32 (s, 6H, 2×CH$_3$); 2.73; 2.91 (CH$_3$, DMF-D7); 3.63-3.69; (m, 6H, 3×CH$_2$); 3.84 (s, 3H, O—CH$_3$); 4.70 (s, 2H, CH$_2$); 5.06 (s, 2H, CH$_2$); 7.14 (m, 3H, 3×CH); 7.49-7.50 (d, 2H, 2×CH); 7.76-7.77 (d, 2H, 2×CH); 8.05 (CH, DMF); 10.99 (s, 1H, NH)

$^{13}$C-NMR (DMF-D7, ppm): 8.82 (CH$_3$); 18.95 (CH$_3$); 29.70-30.71 (DMF-D7); 34.86-35.87 (DMF-D7); 40.54 (CH$_2$); 52.26 (O—CH$_3$); 55.43 (CH$_2$); 56.87 (CH$_2$); 62.52 (CH$_2$); 127.24 (C); 127.83 (CH); 128.63 (CH); 130.84 (CH); 133.91 (CH); 134.65 (C); 136.09 (C); 137.89 (C); 162.53-163.0 (DMF-D7); 163.41 (C); 172.09 (C)

Example 7

Synthesis of 2-(2,6-dimethylphenylamino)-N,N-diethyl-N-(4-(1-methoxy-1-oxopropane-2-yl)benzyl)-2-oxoethane Ammonium Bromide 0.4 g of lidocaine (1.7 mmol) are combined with 0.44 g (1.7 mmol) of methyl-2-(4-(bromomethyl)phenyl)propanoate and shaken several times. Simultaneously, to complete the reaction it is heated for 20 Minutes to 80° C. Subsequently, 10 ml of THE are added and stirred. The white precipitate formed is filtered off, washed with THE and dried. 2-(2,6-Dimethylphenylamino)-N,N-diethyl-N-(4-(1-methoxy-1-oxopropan-2-yl)benzyl)-2-oxoethane ammonium bromide is obtained.

Example 8

Synthesis of 2-(2,6-dimethylphenylamino)-N-(4-(2-ethoxy-2-oxoethylcarbamoyl)benzyl)N,N-diethyl-2-oxoethane Ammonium Bromide 0.39 g of lidocaine (1.7 mmol) are added to 0.5 g of ethyl-2-(4-(bromomethyl)benzamido)acetate (1.7 mmol) and shaken several times at 80° C. within 20 minutes after having been added. Subsequently, 10 ml of THE are added and stirred. The white precipitate formed is filtered off, washed with THE and dried. 2-(2,6-Dimethylphenylamino) N-(4-(2-ethoxy-2-oxoethylcarbamoyl)benzyl)-N,N-diethyl-2-oxoethane ammonium bromide is obtained.

$^1$H-NMR (D$_2$O, ppm): 1.31-1.34 (t, 3H, CH$_3$); 1.53-1.56 (t, 6H, 2×CH$_3$); 2.25 (s, 6H, 2×CH$_3$); 3.58-3.67; (m, 4H, 2×CH$_2$); 4.22 (s, 4H, 2×CH$_2$); 4.27-4.31; (q, 2H, CH$_2$); 4.89

(s, 2H, CH$_2$); 7.20-7.28 (m, 3H, 3×CH); 7.68-7.69 (d, 2H, 2×CH); 7.94-7.96 (d, 2H, 2×CH); $^{13}$C-NMR (D$_2$O, ppm): 8.40 (CH$_3$); 14.38 (CH$_3$); 18.42 (CH$_3$); 42.94 (CH$_2$); 55.69 (CH$_2$); 56.35 (CH$_2$); 62.31 (CH$_2$); 63.59 (CH$_2$); 129.08 (CH); 129.37 (CH); 129.49 (CH); 131.86 (C); 132.98 (C); 134.11 (CH); 136.02 (C); 136.74 (C); 164.70 (C); 170.73 (C); 172.60 (C)

Example 9

Synthesis of 2-(2,6-dimethylphenylamino)-N-(4-(2-(2-ethoxy-2-oxoethylamino)-2-oxoethylcarbamoyl) benzyl)-N,N-diethyl-2-oxoethane Ammonium Bromide 0.23 g of ethyl-2-(2-(4-(bromomethyl)benzamido)acetamido)acetate (0.6 mmol) are combined with 0.15 g of lidocaine (0.6 mmol) and shaken several times at 80° C. within 20 minutes after having been added. Subsequently, 10 ml of THF are added and stirred. The white precipitate formed is filtered off, washed with THF and dried. 2-(2,6-Dimethylphenylamino)-N-(4-(2-(2-ethoxy-2-oxoethylamino)-2-oxoethyl-carbamoyl)benzyl)-N,N-diethyl-2-oxoethane ammonium bromide is obtained.

Example 10

Synthesis of N-(3-carboxybenzyl)-2-(2,6-dimethylphenylamino)-N,N-diethyl-2-oxoethane Ammonium Bromide by Saponification with NaOH An excess of NaOH (3.2 mmol, 129.4 mg) in ethanol is added to 0.5 g of 2-(2,6-dimethylphenylamino)-N,N-diethyl-N-(3-(methoxycarbonyl)benzyl)-2-oxoethane ammonium bromide (1.08 mmol) and heated for three hours to boiling. Subsequently, 25 ml of 0.1 N HCl are added. The solution is evaporated to dryness and the oily product is mixed with THF and stirred. The white precipitate formed is filtered off and washed with THE. N-(3-Carboxybenzyl)-2-(2,6-dimethylphenylamino)-N,N-diethyl-2-oxoethane ammonium bromide is obtained.

m.p.: 142-144° C.

MS: (ESI) m/z=369.217 Da (C$_{22}$H$_{29}$N$_2$O$_3$)$^+$ $^1$H-NMR (D$_2$O+NaOD, ppm): 1.50-1.55 (t, 6H, 2×CH$_3$); 2.13 (s, 6H, 2×CH$_3$); 3.44-3.60 (m, 4H, 2×CH$_2$); 4.89 (s, 2H, CH$_2$+D$_2$O); 4.91 (s, 2H, CH$_2$); 6.94-6.97 (t, 1H, CH); 7.09-7.11 (d, 2H, 2×CH); 7.59-7.62 (t, 1H, CH); 7.80-7.82 (d, 1H, CH); 8.00-8.01 (d, 1H, CH); 8.06 (s, 1H, CH)

$^{13}$C-NMR (D$_2$O+NaOD, ppm): 10.41 (CH$_3$); 20.56 (CH$_3$); 56.35 (CH$_2$); 63.53 (CH$_2$); 70.66 (CH$_2$); 125.54 (CH); 130.32 (CH); 130.51 (C); 131.92 (CH); 133.47 (CH); 133.88 (C); 135.68 (CH); 138.17 (CH); 140.00 (C); 149.15 (C); 163.75 (C); 177.55 (C)

Example 11

Synthesis of N-(3-carboxybenzyl)-2-(2,6-dimethylphenylamino)-N,N-diethyl-2-oxoethane Ammonium Bromide by Saponification with Ba(OH)$_2$ 30 ml of a 0.05 M Ba(OH)$_2$ solution in ethanol is added to 0.5 g of 2-(2,6-dimethylphenylamino)-N,N-diethyl-N-(3-(methoxycarbonyl)benzyl)-2-oxoethane ammonium bromide (1.08 mmol) and heated for three hours to boiling. Subsequently, 30 ml of a 0.05 M H$_2$SO$_4$ solution are added. The precipitate mainly consisting of BaSO$_4$ is filtered off. Subsequently, the solution is evaporated to dryness and the crystalline product is washed with THE. N-(3-Carboxybenzyl)-2-(2,6-dimethylphenylamino)-N,N-diethyl-2-oxoethane ammonium sulphate.

Example 12

Coupling of N-(3-carboxybenzyl)-2-(2,6-dimethylphenylamino)-N,N-diethyl-2-oxoethane Ammonium Bromide with the Peptide (Fmoc)G-P-Q-G-I-A-G-Q-A(N3)-Q Resin (SEQ ID NO: 1)

The peptide (Fmoc)G-P-Q-G-I-A-G-Q-A(N$_3$)-Q resin (SEQ ID NO: 1) is gradually synthesized on a synthesis resin by means of common peptide synthesis (Fmoc strategy). To attach the bitter principle the Fmoc protective group of the N-terminal terminal amino acid glycine is cleaved-off by means of 40% and 20% piperidine solution in DMF. 83.5 mol of the denatonium derivative are dissolved in 500 µl of a 0.5 M HOBt solution of H$_2$O/DMF 1:4. To the resin there is added the solution and subsequently 20 µl of diisopropylcarbodiimide (DIC) and shaken for one hour at room temperature. Subsequently, the resin is washed several times with DMF, dichloromethane, and diethyl ether. A resin-bound peptide-bitter principle coupling product is obtained.

After coupling, the protective groups as well as the product consisting of denatonium derivative and peptide are simultaneously cleaved-off from the carrier with the addition of TFA. Reactive carbocations formed during the cleavage are quenched by the scavengers ethane dithiol, metacresol, and thioanisole.

Subsequently, the denatonium derivative/peptide construct cleaved-off from the carrier is precipitated in ice-cold ether and after centrifugation the solution is removed from the pellet formed. Coupling can be verified by means of mass spectrometry (electrospray ionization (ESI) or matrix-assisted laser desorption/ionization (MALDI)).

Example 13

Coupling of N-(3-carboxybenzyl)-2-(2,6-dimethylphenylamino)-N,N-diethyl-2-oxoethane Ammonium Bromide with the Peptide (Fmoc)G-P-Q-G-I-A-G-Q-A(N3)-Q Resin (SEQ ID NO: 1)

The peptide (Fmoc)G-P-Q-G-I-A-G-Q-A(N$_3$)-Q resin (SEQ ID NO: 1) is stepwise synthesized on a synthesis resin by means of common peptide synthesis (Fmoc strategy). To attach the bitter principle the Fmoc protective group of the N-terminal terminal amino acid glycine is cleaved-off by means of 40% and 20% piperidine solution in DMF. 83.5 µmol of the denatonium derivative are dissolved in 500 µl of a 0.5 M HOBt solution of H$_2$O/DMF 1:4. To the resin there is added the solution and subsequently a solution of 125 µmol of N-ethyl-N'-(3-dimethylaminopropyl)carbodiimide hydrochloride (EDC) in 100 µl H$_2$O/DMF 1:4 and shaken for one hour at room temperature. Subsequently, the resin is washed several times with DMF, dichloromethane, and diethyl ether. A resin-bound peptide-bitter principle coupling product is obtained.

After coupling, the protective groups as well as the product consisting of denatonium derivative and peptide are simultaneously cleaved-off from the carrier with the addition of TFA. Reactive carbocations formed during the cleavage are quenched by the scavengers ethane dithiol and thioanisole.

After an incubation time of 1.5 hours the denatonium derivative/peptide construct cleaved-off from the carrier is precipitated in ice-cold ether and after centrifugation the solution is removed from the pellet formed. Coupling can be verified by means of mass spectrometry (electrospray ionization (ESI) or matrix-assisted laser desorption/ionization (MALDI)).

Example 14

Coupling of N-(3-carboxybenzyl)-2-(2,6-dimethylphenylamino)-N,N-diethyl-2-oxoethane ammonium bromide with the peptide (Fmoc)NH-PEG(3)-Lys(Boc)-G-P-Q-G-1-A-G-Q-PEG(3)-Q resin (SEQ ID NO: 2)

The peptide (Fmoc)NH-PEG(3)-Lys(Boc)-G-P-Q-G-1-A-G-Q-PEG(3)-Q resin (SEQ ID NO: 2) is gradually synthesized on a synthesis resin by means of common peptide synthesis (Fmoc strategy). To attach the bitter principle the Fmoc protective group of the terminal amino acid $NH_2$—PEG(3)—COOH is cleaved-off by means of 40% and 20% piperidine solution in DMF. 83.5 µmol of the denatonium derivative are dissolved in 500 µl of a 0.5 M HOBt solution of $H_2O$/DMF 1:4. To the resin there is added the solution and subsequently 20 µl of diisopropylcarbodiimide (DIC) and shaken for one hour at room temperature. Subsequently, the resin is washed several times with DMF, dichloromethane, and diethyl ether. A resin-bound peptide-bitter principle coupling product is obtained.

After coupling, the protective groups as well as the product consisting of denatonium derivative and peptide are simultaneously cleaved-off from the carrier with the addition of TFA. Reactive carbocations formed during the cleavage are quenched by the scavengers ethane dithiol, metacresol, and thioanisole.

After an incubation time of 1.5 hours the denatonium derivative/peptide construct cleaved-off from the carrier is precipitated in ice-cold ether and after centrifugation the solution is removed from the pellet formed. Coupling can be verified by means of mass spectrometry (electrospray ionization (ESI) or matrix-assisted laser desorption/ionization (MALDI)).
MS (MALDI-TOF): m/z=1739

Example 15

Coupling of N-(3-carboxybenzyl)-2-(2,6-dimethylphenylamino)-N,N-diethyl-2-oxoethane Ammonium Bromide with the Peptide (Fmoc)NH-PEG(3)-Lys(Boc)-G-P-Q-G-1-A-G-Q-PEG(3)-A($N_3$)-Q Resin (SEQ ID NO: 3)

The peptide (Fmoc)NH-PEG(3)-Lys(Boc)-G-P-Q-G-1-A-G-Q-PEG(3)-A($N_3$)-Q resin (SEQ ID NO: 3) is gradually synthesized on a synthesis resin by means of common peptide synthesis (Fmoc strategy). To attach the bitter principle the Fmoc protective group of the terminal amino acid $NH_2$—PEG(3)—COOH is cleaved-off by means of 40% and 20% piperidine solution in DMF. 83.5 µmol of the denatonium derivative are dissolved in 500 µl of a 0.5 M HOBt solution of $H_2O$/DMF 1:4. To the resin there is added the solution and subsequently 20 µl of diisopropylcarbodiimide (DIC) and shaken for one hour at room temperature. Subsequently, the resin is washed several times with DMF, dichloromethane, and diethyl ether. A resin-bound peptide-bitter principle coupling product is obtained.

After coupling, the protective groups as well as the product consisting of denatonium derivative and peptide are simultaneously cleaved-off from the carrier with the addition of TFA. Reactive carbocations formed during the cleavage are quenched by the scavengers ethane dithiol, metacresol, and thioanisole.

After an incubation time of 1.5 hours the denatonium derivative/peptide construct cleaved-off from the carrier is precipitated in ice-cold ether and after centrifugation the solution is removed from the pellet formed. Coupling can be verified by means of mass spectrometry (electrospray ionization (ESI) or matrix-assisted laser desorption/ionization (MALDI)).
MS (MALDI-TOF): m/z=1852

Example 16

Enzymatic Peptide Cleavage 1

The peptides listed in examples 12-15 can be specifically cleaved after having been cleaved-off from the resin by matrix metalloproteinases (MMP) such as MMP-8. For that, a 2-3 hour activation of the pre-MMP by p-aminophenyl mercury acetate (APMA 10 mM in 0.1 M NaOH) in a ratio of 10:1 (MMP:APMA v/v) takes place at 37° C. Subsequently, the activated MMP is added to the peptides dissolved in buffer (200 mM NaCl, 50 mM Tris-HCl, 5 mM $CaCl_2$, 1 µM $ZnCl_2$, 0.05% BRIJ® 35, 0.05% $NaN_3$, pH 7.0) in defined concentrations (9 ng/ml, 45 ng/ml, 90 ng/ml, 225 ng/ml, 450 ng/ml, and 900 ng/ml) and incubated for 1 h at 37° C. The reaction is stopped by separation/filtration of the MMP by centrifugation or addition of 10 equivalents of EDTA (250 mM). The cleavage products are analyzed by liquid chromatography with masse spectrometry coupling (LC-MS).

Example 17

Enzymatic Peptide Cleavage II

The peptide NH2-G-p-q-G-I-A-G-q-Q—COOH (small letters mean D-amino acids) (SEQ ID NO:4) modified by replacing L by D amino acids is specifically cleaved after having been cleaved-off from the resin by MMPs such as MMP-8. For that, a 2-3 hour activation of the pre-MMP by p-aminophenyl mercury acetate (APMA 10 mM in 0.1 M NaOH) in a ratio of 10:1 (MMP:APMA v/v) takes place at 37° C. Subsequently, the activated MMP is added to the peptides dissolved in buffer (200 mM NaCl, 50 mM Tris-HCl, 5 mM $CaCl_2$, 1 µM $ZnCl_2$, 0.05% BRIJ® 35, 0.05% $NaN_3$, pH 7.0) in defined concentrations and incubated for 1 h at 37° C. The reaction is stopped by separation/filtration of the MMP by centrifugation or addition of 10 equivalents of EDTA (250 mM). The cleavage products are analyzed by liquid chromatography with mass spectrometry coupling (LC-MS).

Example 18

Taste testing by means of an electronic tongue of 2-(2,6-dimethylphenylamino)-N,N-diethyl-N-(3-(methoxycarbonyl)benzyl)-2-oxoethane Ammonium Bromide The potentials of aqueous solutions of the substance are compared with denatonium benzoate (in brackets) by means of an electronic tongue and are in a range of about: type of sensor SB2AC0: 0.05 mM=−75 mV (−75 mV); 0.1 mM=−65 mV (−61.5 mV); 0.5 mM=−32 mV (−30 mV); 1 mM=−

20 mV (−24 mV); type of sensor SB2AN0: 0.05 mM=−90 mV (−90 mV); 0.1 mM=−88.5 mV (−85 mV); 0.5 mM=−60 mV (−60 mV); 1 mM=−21.5 mV (−26 mV); type of sensor SB2BT0: 0.05 mM=−73 mV (−72 mV); 0.1 mM=−72 mV (−54 mV); 0.5 mM=7 mV (−2 mV); 1 mM=44 mV (47 mV). The electrical potentials measured indicate a strongly bitter substance.

Example 19

Taste Testing by Means of an Electronic Tongue of 2-(2,6-Dimethylphenylamino)N-(4-(2-ethoxy-2-oxoethylcarbamoyl)benzyl)-N,N-diethyl-2-oxoethane Ammonium Bromide The potentials of aqueous solutions of the substance are compared with denatonium benzoate (in brackets) by means of an electronic tongue and are in a range of about: type of sensor SB2AC0: 0.05 mM=−93 mV (−72 mV); 0.1 mM=−88 mV (−57 mV); 0.5 mM=−52-mV (−23 mV); 1 mM=−42 mV (−6 mV); type of sensor SB2AN0: 0.05 mM=−70 mV (−60 mV); 0.1 mM=−60 mV (−50 mV); 0.5 mM=−30 mV (−1 mV); 1 mM=−10 mV (20 mV); type of sensor SB2BT0: 0.05 mM=−95 mV (−80 mV); 0.1 mM=−94 mV (−62 mV); 0.5 mM=−35 mV (7 mV); 1 mM=5 mV (42 mV). The electrical potentials indicate a strongly bitter substance.

Example 20

Synthesis of 2-(2,6-dimethylphenylamino)-N,N-diethyl-N-(3-methoxybenzyl)-2-oxoethane Ammonium Bromide 1 g of lidocaine (4.3 mmol) is combined with 0.86 g (4.3 mmol) of 3-methoxybenzyl bromide and shaken several times at room temperature within 20 minutes after having been added. Subsequently, 10 ml of THE are added and stirred. The white precipitate formed is filtered off, washed with THE and dried. 2-(2,6-Dimethylphenylamino)-N,N-diethyl-N-(3-methoxybenzyl)-2-oxoethane ammonium bromide is obtained.

m.p.: 144-151° C.

$^1$H-NMR (CDCl$_3$. ppm): 1.52-1.55 (t, 6H, 2×CH$_3$); 2.27 (s, 6H, 2×CH$_3$); 3.45-3.52 (qd, 2H, CH$_2$); 3.59-3.66 (qd, 2H, CH$_2$); 3.81 (s, 3H, CH$_3$); 4.65 (s, 2H, CH$_2$); 4.85 (s, 2H, CH$_2$); 7.02-7.11 (m, 6H, CH); 7.35-7.38 (m, 1H, CH); 10.48 (s, 1H, NH)

Example 21

Synthesis of 2-(2,6-dimethylphenylamino)-N,N-diethyl-N-(3-hydroxybenzyl)-2-oxoethane Ammonium Bromide 0.5 g of 2-(2,6-dimethylphenylamino)-N,N-diethyl-N-(3-methoxybenzyl)-2-oxoethane ammonium bromide (1.1 mmol) are dissolved in 10 ml of dichloromethane and stirred. A solution of borontribromide (2.3 mmol) in 10 ml of methylenechloride at −70° C. is added dropwise. When reaching room temperature 5 ml of water are added to the mixture. The organic phase is evaporated and purified by column chromatography over aluminumoxide (eluant: methanol/chloroform 1:9). 2-(2,6-Dimethylphenylamino)-N,N-diethyl-N-(3-hydroxybenzyl)-2-oxoethane ammonium bromide is obtained.

Example 22

Synthesis of 2-(2,6-dimethylphenylamino)-N,N-diethyl-N-(tert-butyl-4-(bromomethyl)-phenylcarbamate)-2-oxoethane Ammonium Bromide 0.5 g of lidocaine (2.1 mmol) are combined with 0.61 g (2.1 mmol) of tert-butyl-4-(bromomethyl)phenylcarbamate and shaken several times. Simultaneously, to complete the reaction it is heated for 20 minutes to 80° C. Subsequently, 10 ml of THE are added and stirred. The white precipitate formed is filtered off, washed with THE and dried. 2-(2,6-Dimethylphenylamino)-N,N-diethyl-N-(tert-butyl-4-(bromomethyl)-phenylcarbamate)-2-oxoethane ammonium bromide is obtained.

Example 23

Synthesis of 2-(2,6-dimethylphenylamino)-N,N-diethyl-N-4-(aminobenzyl)-2-oxoethane Ammonium Bromide 0.5 g of 2-(2,6-dimethylphenylamino)-N,N-diethyl-N-(tert-butyl-4-(bromomethyl)-phenylcarbamate)-2-oxoethane ammonium bromide (0.96 μmol) are stirred with 1.9 μmol of trifluoroacetic acid in 10 ml of methylenechloride. The organic phase is evaporated and purified by column chromatography over aluminumoxide (eluant:methanol/chloroform 1:9). 2-(2,6-Dimethylphenylamino)-N,N-diethyl-N-4-(aminobenzyl)-2-oxoethane ammonium bromide is obtained.

The invention claimed is:
1. A compound of general formula 1

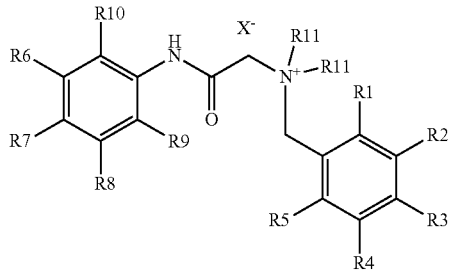

Formula 1 wherein:
(i) X⁻ represents halogenide, sulphate, benzoate, acetate, trifluoroacetate, hydroxide, saccharinate, or capsaicinate,
(ii) R1-R10 independently represent:
  (a) hydrogen,
  (b) halogen,
  (c) C1-C5 alkyl,
  (d) C1-C4 alkoxy,
  (e) C1-C20 alkoxycarbonyl
  (f) —NH—P or —O—P, wherein P is a hydrogen or a residue consisting of 1-30 amino acids selected from the group consisting of D-amino acids, L-amino acids and unnatural amino acids, wherein said amino acids are optionally modified for coupling,
  (g) —(Y)$_n$—COOM with M=Na, K, or [N(R12)$_4$]⁺, or
  (h) —(Y)$_n$—C(O)NR14R15, further wherein Y represents an organic residue selected from the group consisting of: —CH$_2$—, —CH(CH$_3$)—, —CH$_2$—CH$_2$—, —(CH$_2$)$_3$—, —CH=CH—, —C≡C—, —O—CH$_2$—CH$_2$—, —O—CH$_2$—CH$_2$—O—CH$_2$—CH$_2$—, and —NH—CH$_2$—CH$_2$— and n=0 or 1,
(iii) R14 and R15 represent hydrogen, a C1-C12 alkyl, or a residue consisting of 1-30 amino acids selected from the group consisting of D-amino acids, L-amino acids and unnatural amino acids, and
(iv) at least one of the residues R1-R10 is a (a) —(Y)$_n$—COOM or (b) —(Y)$_n$—C(O)NR14R15, wherein Y, M, R14, and R15 are as defined above, and
(v) R11 and R12 independently represent hydrogen or a C1-C10 alkyl residue.

2. The compound according to claim 1, wherein, in the general formula 1:
(i) residue R11 is an ethyl group,
(ii) residues R9 and R10 are methyl groups,
(iii) residues R1, R4, R5, R6, R7, and R8 represent hydrogen, and
(iv) one of residues R2 and R3 represents hydrogen and the other is selected from the group consisting of;
  (a) —(Y)$_n$—COOM with M=Na, K, or [N(R12)$_4$]⁺, and
  (b) —(Y)$_n$—C(O)NR14R15,
or residues R2 and R3 independently represent:
  (a) —(Y)$_n$—COOM with M=Na, K, or [N(R12)$_4$]⁺, or
  (b) —(Y)$_n$—C(O)NR14R15, wherein Y, M, R14, and R15 are as defined in claim 1, further wherein:
    a. residues R14 and R15 independently represent hydrogen, a C1-C12 alkyl or a residue consisting of 1-30 amino acids selected from the group consisting of D-amino acids, L-amino acids and unnatural amino acids, residue R12 represents hydrogen or a C1-C10 alkyl residue.

3. A substrate comprising a compound according to claim 1, bound to a substrate surface fabricated of a metal, ceramic, glass, or polymeric material via one of residues R1-R10 of said compound.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (9)..(9)
<223> OTHER INFORMATION: Ala(N3)

<400> SEQUENCE: 1
```

```
Gly Pro Gln Gly Ile Ala Gly Gln Ala Gln
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (Fmoc)NH-PEG(3)
<220> FEATURE:
<221> NAME/KEY: MOD_RES
<222> LOCATION: (1)..(1)
<223> OTHER INFORMATION: Lys(Boc)
<220> FEATURE:
<223> OTHER INFORMATION: C-term PEG(3)

<400> SEQUENCE: 2

Lys Gly Pro Gln Gly Ile Ala Gly Gln
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (Fmoc)NH-PEG(3)
<220> FEATURE:
<221> NAME/KEY: MOD_RES
<222> LOCATION: (1)..(1)
<223> OTHER INFORMATION: Lys(Boc)
<220> FEATURE:
<223> OTHER INFORMATION: C-term PEG(3)

<400> SEQUENCE: 3

Lys Gly Pro Gln Gly Ile Ala Gly Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 4

Gly Pro Gln Gly Ile Ala Gly Gln Gln
1               5
```